(12) United States Patent
Huszar

(10) Patent No.: US 6,541,206 B1
(45) Date of Patent: Apr. 1, 2003

(54) OBJECTIVE BIOCHEMICAL METHOD FOR ASSESSMENT OF SPERM QUALITY

(75) Inventor: Gabor B. Huszar, 16 Chestnut La., Woodbridge, CT (US) 06525

(73) Assignee: Gabor B. Huszar, Woodbridge, CT (US)

( * ) Notice: Subject to any disclaimer, the term of this patent is extended or adjusted under 35 U.S.C. 154(b) by 0 days.

(21) Appl. No.: 09/595,666

(22) Filed: Jun. 19, 2000

(51) Int. Cl.$^7$ .................. G01N 33/543; G01N 33/554; A01N 1/02; C12Q 1/68

(52) U.S. Cl. .............. 435/6; 435/2; 435/7.21; 435/7.8; 435/7.94; 435/7.95; 435/332; 435/334; 435/806; 435/975; 436/503; 436/518; 436/519; 436/63; 436/172; 530/388.2; 530/388.22; 530/852

(58) Field of Search ................. 435/2, 6, 7.1, 7.21, 435/7.8, 7.92, 7.94, 7.95, 17, 194, 334, 806, 975, 332; 436/503, 518, 519, 536, 63, 172, 906; 530/350, 388.2, 388.22, 852

(56) References Cited

U.S. PATENT DOCUMENTS 4,945,044 A 7/1990 Huszar

OTHER PUBLICATIONS

Dix et al., 1996. Targeted gene disruption of Hsp70–2 results in failed meiosis, germ cell apoptosis, and male infertility. Proc. Natl. Acad. Sci. USA 93: 3264–3268.*
Eddy, 1999. Role of heat shock protein HSP70–2 in spermatogenesis. Rev. Reprod. 4: 23–30.*
Harlow et al., 1988. *Antibodies. A Laboratory Manual*, Cold Spring Harbor Laboratory, Cold Spring Harbor. pp. 553–612.*
Raab et al., 1995. Characterization of the heat shock protein P70 in rat spermatogenic cells. Mol. Reprod. Develop. 40: 186–195.*
Gabor Huszar, Marcelia Corrales and Lynne Vigue; Correlation Between Sperm Creatine Phosphokinase Activity and Sperm Concentrations In Normospermic and Oligospermic Men, Gamete Research, 19: 67–75; accepted Sep. 15, 1987, pp. 67–75, copyright 1988.
Gabor Huszar, Lynne Vigue and Marcelia Corrales; Sperm Creatine Phosphokinase Activity as a Measure of Sperm Quality in Normospermic, Variablespermic, and Oligospermic Men, Biology of Reproduction 38, pp. 1061–1066 (1988).
Gabor Huszar, Lynne Vigue and Melanie Willets; CPK Activity and Isoform Ratios in Stallion Sperm; American Society of Andrology, 1989 Annual Meeting, Apr. 13–16, 1989 1 page.
Gabor Huszar, M.D., Lynne Vigue, M.D., and Marcelia Corrales, M.D., Sperm Creatine Kinase Activity in Fertile and Infertile Oligospermic Men; Reprinted form Journal of Andrology, Jan.–Feb. 1990, vol. 11, No. 1, pp. 40–46.

Gabor Huszar and Lynne Vigue, Spermatogenesis–Related Change in the Synthesis of the Creatine Kinase B–Type and M–Type Isoforms in Human Spermatozoa; Molecular Reproduction and Development 25:258–262, 1990, pp. 258–262.
Gabor Huszar, M.D., Lynne Vigue, M.S., Mahmood Morshedi, M.D.; Sperm Creatine Phosphokinase M–Isoform Ratios and Fertilizing Potential of Men: a Blinded Study of 84 Couples Treated With In Vitro Fertilization; Fertiliey and Sterility vol., 57, No. 4, Apr. 1992, pp. 882–888.
Gabor Huszar, Lynne Vigue; Incomplete Development of Human Spermatozoa Is Associated With Increased Creatine Phosphokinase Concentration and Abnormal Head Morphology, Molecular Reproduction and Development 34:292–298 (1993), pp. 292–298.
Gabor Huszar, M.D., Lynne Vigue, M.S., Sergio Oehninger, M.D.; Creatine Kinase Immunocytochemistry of Human Sperm–Hemizona Complexes: Selective Binding of Sperm With Mature Creatine Kinase–Staining Pattern; Fertility and Sterility, vol. 61, No. 1, Jan. 1994, pp. 136–142.
Gabor Huszar and Lynne Vigue; Correlation Between the Rate of Lipid Peroxidation and Cellular Maturity as Measured by Creatine Kinase Activity in Human Spermatozoa, Journal of Andrology, vol. 15, No. 1, Jan./Feb. 1994, pp. 71–77.
Gabor Huszar; The Role of Sperm Creatine Kinase in the Assessment of Male Fertility, Reproductive Medicine Review 1994; 3:179–197, pp. 179–197.
G. Huszar, S. Kliesch, L. Vigue, HM Behre; Both Sperm Concentration and Sperm Fertilizing Potential Decline in Men Receiving the GnRH Antagonist Cetrorelix for Contraception, Abstract, American Society for Reproductive Medicine, Oct. 7–12, 1995, 1 page.

(List continued on next page.)

*Primary Examiner*—Bao-Thuy L. Nguyen
*Assistant Examiner*—James L. Grun
(74) *Attorney, Agent, or Firm*—DeLio & Peterson, LLC

(57) ABSTRACT

A method of testing sperm quality including obtaining a sample of sperm to be tested; detecting and measuring the testis-specific HspA2 chaperone protein (or, the chaperone protein homologues to HspA2) in human and animal sperm; and determining a sperm quality parameter based upon the chaperone protein, wherein an increased amount of the chaperone protein species indicates a higher sperm quality. The chaperone protein is detected and measured either by binding one or more antibodies specific to the sperm chaperone protein to the sperm and measuring the antibody content or measuring ATP bound to the sperm chaperone protein. In the case of the latter method, the chaperone protein may be detected and measured by measuring ATP bound to the sperm chaperone protein, and such measuring is by chaperone protein-bound and CK-B generated ATP measurement, or by bioluminescence of the chaperone protein bound-ATP.

22 Claims, No Drawings

OTHER PUBLICATIONS

Y. Yamada, L. Vigue, G. Huszar; Sperm Creatine Kinase (CK) Parameters and Strict Sperm Morphology in Men: Relationship Between the Biochemical and Morphological Measures of Sperm Maturity and Fertilizing Potential, Abstract, American Society for Reproductive Medicine, Oct. 7–12, 1995, 1 page.

Gabor Huszar, Marco Sbracia, Lynne Vigue, David J. Miller and Barry D. Shur, Sperm Plasma Membrane Remodeling During Spermiogenetic Maturation in Men; Relationship Among Plasma Membrane β1,4–Galactosyltransferase, Cytoplasmic Creatine Phosphokinase, and Creatine Phosphokinase Isoform Ratios, Biology of Reproduction 56, 1997, pp. 1020–1024.

Andrew J. Wyrobek, Steven M. Schrader, Sally D. Perreault, Laura Fenster, Gabor Huszar, David F. Katz, Ana Maria Osorio, Virginia Sublet, and Donald Evenson; Assessment of Reproductive Disorders and Birth Defects in Communities near Hazardous Chemical Sites. III. Guidelines for Field Studies of Male Reproductive Disorders, Reproductive Technology, 1997, vol. 11, Nos. 2/3, pp. 243–259.

E. Moretti, A. Gergely, H.B. Zeyneloglu, P. Ward, D. Ward, B. Baccetti, G. Huszar; Relationship Among Head Size, Morphology and Chromosome Structure in Human Spermatozoa, American Society of Reproductive Medicine, Oct./Nov. 1997, 1 page.

Gabor Huszar, Jamie Arruda, Istvan Marton, Barbara Villaccio and Hulusi Zeyneloglu; Correlation Between Diminished Sperm Maturity and Increased Rate of DNA Degradation in Human Spermatozoa, Meeting of the Australian Fertility Society, Sep. 1998, 1 page.

G. B. Huszar, E.L. Gordon, D.S. Irvine, R.J. Aitken; Absence of DNA Cleavage in Mature Human Sperm Selected by Their Surface Membrane Receptors, Abstract, American Society for Reproductive Medicine, Nov. 1998, 1 page.

Grace Kawas Lemasters, Donna M. Olsen, James H. Yiin, James E. Lockey, Rakesh Shukla, Sherry G. Selevan, Steve M. Schrader, Greg P. Toth, Donald P. Evenson and Gabor B. Huszar; Male Reproductive Effects of Solvent and Fuel Exposure During Aircraft Maintenance, Reproductive Toxicology, 1999, vol. 13, No. 3, pp. 155–166.

Anna Gergely, Ertug Kovanci, Levent Senturk, Eric Cosmi, Lynne Vigue, Gabor Huszar; Morphometric Assessment of Mature and Diminished–Maturity Human Spermatozoa: Sperm Regions that Reflect Differences in Maturity, Human Reproduction, 1999, vol. 14, No. 8, pp. 2007–2014.

G. Huszar, K. Stone, L. Vigue; The Putative Human Sperm Creatine Kinase M–Isoform (CK–M) is 64kDa Heat Shock Protein, Homologous to the HSP70–2: Characterization by Primary Structure and Testicular Expression Pattern, Abstract, 15th Annual Meeting of the ESHRE, 1999, 1 page. Human Reprod. 14 (Abst. Book 1): 84.

Gabor Huszar, Kathryn Stone, David Dix, and Lynne Vigue, Putative Creatine Kinase M–Isoform in Human Sperm is Identified as the 70–Kilodalton Heat Shock Protein HspA2[1], Biology of Reproduction, 63, Apr. 2000, pp. 925–932.

E. Kovanci, L. Vigue, P. Bray–Ward, DC Ward, G. Huszar; Lack of the HSP70–2 Chaperone is Associated with Meiotic Defects and Cytoplasmic Retention in Human Sperm: Relationship Between Chromosomal Aneuploidy and Sperm Immaturity, Abstract, American Society for Reproductive Medicine, Oct. 21–25, 2000, 1 page.

* cited by examiner

OBJECTIVE BIOCHEMICAL METHOD FOR ASSESSMENT OF SPERM QUALITY

BACKGROUND OF THE INVENTION

1. Field of the Invention

This invention relates to a biochemical method for determining the fertilization potential in sperm and, in particular, to a method which utilizes the measurement of particular proteins in spermatozoa which reflect sperm development, maturity, DNA integrity and fertility.

2. Description of Related Art

The testicle serves as site for spermatogenesis, sperm production and sperm maturation. Diagnosis of possible problems in spermatogenesis is normally carried out with the determination of sperm concentrations in the ejaculate. The sperm count fluctuates in all men, but the fluctuations are more detectable in oligospermic (OS) men with sperm counts below the $20 \times 10^6$ sperm/ml semen of normal or "normospermic" (NS) level. Low sperm concentrations may be a consequence of pituitary problems, deficient hormone levels, testicular disorders and diminished sperm production, retrograde ejaculation, partial obstruction of the ejaculatory tract, age, environmental factors, fever or excess heat, exposure to organic solvents in the work place, etc.

It has been shown that male factor is a contributory cause of infertility in about 40% to 50% of the couples. The overwhelming majority of these infertile and subfertile men are oligospermic and/or asthenospermic (sperm motility is lower than 50%). Management problems exist with respect to these infertile men, as these men may try to father children for years without success. With intrauterine placement of the sperm the pregnancy rates for couples with male factor infertility are only about 15–20% per cycle. This is in spite of the fact that there is no detectable difference in sperm concentrations and motility among the groups of husbands who do or do not cause pregnancy following intrauterine insemination treatment. The pregnancy rates with in vitro fertilization treatment are higher, but adequate sperm concentration or sperm motility does not assure the occurrence of pregnancies. There are also men who suffer from unexplained male infertility, i.e. sperm with diminished fertility in spite of normal sperm concentrations.

Beyond the classical semen analysis parameters, i.e., sperm concentration, motility and velocity, present approaches to evaluate selected sperm functions include the assessment of motile sperm yield following migration or "swim-up"; measurements of acrosine activity, i.e., the enzyme which facilitates sperm penetration; the hypoosmotic sperm swelling procedure which probes the integrity of the sperm membrane, the sperm-hemizona assay which tests the ability of sperm to bind to segments of human oocytes, the sperm chromatin structure assay; the human sperm zona-free hamster oocyte penetration test, which is more consistent on the negative side (e.g. penetration rates below 15–20% and diminished success in human in vitro fertilization) than it is a measure of fertility. None of these tests, with the exception of the hemi-zona assay, address the overall physiological soundness of the spermatozoa or showed a high correlation with fertilizing potential or occurrence of pregnancies.

It became increasingly apparent that a new approach was necessary for the assessment of sperm fertility/infertility. This new approach was based on measurement of objective sperm biochemical parameters which were shown to have an essential role in the management of male infertility. Such a method for testing sperm quality and fertilizing potential was developed and disclosed in U.S. Pat. No. 4,945,044, "Objective Biochemnical Method for Determining Fertilization Potential in Oligospermic Men" by the inventor of the present application. This method comprised obtaining a sperm sample; detecting the CK enzyme isoforms from the sperm sample, measuring a first CK enzyme concentration for CK-X isoform of the CK enzyme; and determining the sperm quality parameter based upon the first CK enzyme concentration. A second CK enzyme isoform, the CK-B was also measured as a basis for determining the sperm quality parameter. Measurements of the levels of CK-X and CK-B isoforms by electrophoresis and fluorescence visualization technique were used to establish the first and second enzyme concentrations. The sperm quality parameter, as expressed (% CK-X/(CK-X+CK-B)) was proportional to the ratio of the CK-X isoform level to the sum of CK-X and CK-B isoform levels. Sperm fractions which met a predetermined minimum sperm quality level were deemed to be of adequate fertility and selected for use in vivo or in vitro fertilization attempts on oocytes. The validity and predictive value of CK-X/CK-M ratio has been demonstrated in several clinical studies.

Despite the increase in accuracy of the sperm quality parameter described in the '044 patent, the method of testing for the CK-X isoform of the CK enzyme in sperm requires an electrophoretic analysis which is not readily available outside of laboratories. Cost pressures in health care, including reproductive health care, have encouraged the development of tests which do not require relatively expensive laboratory analysis. Sperm quality tests which could be performed in physicians' offices, at relatively lower cost and with more readily available equipment, would represent a great advance in fertility treatment.

Bearing in mind the problems and deficiencies of the prior art, it is therefore an object of the present invention to provide an improved method for testing of sperm quality, which also shows high correlation with fertilizing potential and occurrence of pregnancies.

It is another object of the present invention to provide a method and kit for testing sperm quality which may be readily performed outside of a laboratory environment.

A further object of the invention is to provide a sperm quality test which may be performed at lower cost and in physicians' offices.

Still other objects and advantages of the invention will in part be obvious and will in part be apparent from the specification.

SUMMARY OF THE INVENTION

The above and other objects, which will be apparent to those skilled in the art, are achieved in the present invention which provides, in one aspect, a method of testing sperm quality comprising obtaining a sample of sperm to be tested; detecting and measuring amount of testis-specific chaperone protein in the sperm; and determining a sperm quality parameter based upon the amount of chaperone protein, wherein an increased amount of the chaperone protein indicates a higher sperm quality. Preferably, the chaperone protein is detected and measured either by binding one or more antibodies specific to the sperm chaperone protein to the sperm and measuring the antibody content or measuring ATP bound to the sperm chaperone protein. In the case of the latter method, the chaperone protein may be detected and easured by measuring ATP bound to the sperm chaperone protein, and such easuring is by chaperone protein-bound and CK-B generated ATP measurement, or by haperone protein ATP bioluminescence. Preferably, the chaperone protein is detected and measured by a chaperone protein-specific immuno-assay to determine ATP bound to the sperm chaperone protein.

The preferred method further includes detecting and measuring the amount of ATP generated by the CK-B enzyme in the sperm, and comparing the amount of testis-specific chaperone protein detected and measured in the sperm to the amount of ATP bound to CK-B enzyme detected and measured in the sperm. This provides a ratio of sperm containing the testis-specific chaperone protein to sperm CK-B enzyme, which is used to determine the sperm quality parameter. The chaperone protein may be detected and measured by enzymatic determination of the sperm ATP, with and without CK substrate, in order to measure the chaperone protein-bound ATP versus ATP generated by the sperm CK-B, or by chemical measurement of the chaperone protein-bound ATP in sperm.

Any of these detection methods preferably further include measuring the total amount of sperm in the sample and comparing the amount of testis-specific chaperone protein detected and measured in the sperm to the total sperm to provide a concentration of sperm containing the testis-specific chaperone protein which is used to determine the sperm quality parameter. The total amount of sperm in the sample may be measured by measuring sperm concentration, sperm cytoplasmic protein content, total sperm protein content or sperm DNA. In the case of the latter, the total amount of sperm in the sample may be measured by measuring sperm DNA by colorimetry.

Where the amount of chaperone protein is determined by immuno-assay, a minimum sperm quality parameter is preferably determined to be at least about 10 $\mu$g per mg of sperm protein, or per $10^8$ sperm. Where the amount of chaperone protein is determined by comparing the amount of ATP bound to the testis-specific chaperone protein in the sperm to the amount of ATP generated by CK-B enzyme in the sperm, a minimum sperm quality parameter is preferably determined to be at least about 10% of ATP bound to the testis-specific chaperone protein as compared to ATP generated by CK-B enzyme. Where the amount of chaperone protein is determined by measuring ATP bound to the sperm chaperone protein, a minimum sperm quality parameter is preferably determined to be at least about 0.2 n M of ATP per mg of sperm protein, or per $10^8$ sperm.

The sperm quality parameter is used to predict one or more of the following: i) sperm fertility independently from sperm concentration in semen; ii) sperm maturity changes in men who are treated with male contraceptive methods, independently from sperm concentration in semen; iii) sperm maturity changes in men who are exposed to reproductive toxicity, independently from sperm concentration in semen; iv) extent of sperm cytoplasmic retention; v) sperm plasma membrane remodeling; vi) ability of the sperm to bind to the zona pellucida of oocytes; vii) sperm morphology; viii) level of sperm lipid peroxidation; ix) sperm DNA integrity or extent of sperm DNA fragmentation; x) frequency of sperm chromosomal aneuploidies; and xi) ability of sperm to maintain viability following cryopreservation and thawing.

In another aspect of the present invention, there is provided a method of screening sperm comprising: obtaining a sample of sperm to be tested; detecting presence of testis-specific chaperone protein in one or more individual sperm in the sample; and segregating the sperm based upon presence of the sperm chaperone protein, wherein presence of the chaperone protein indicates a higher sperm quality. The chaperone protein may be detected by binding one or more antibodies specific to the chaperone protein to the sperm or measuring ATP bound to any sperm chaperone protein.

In one preferred method applicable to humans, the chaperone protein is detected by binding one or more HspA2-specific antibodies to the sperm chaperone protein, labeling the HspA2-specific antibodies to which chromophores are conjugated, and observing the chromophore-immuno-labeled sperm, visually or with automated, computer assisted semen analysis. The chromophore-immuno-labeled sperm may be detected in semen, in sperm fractions, in sperm smears, or in tissues or fluids of the male or female reproductive tract.

Individual ejaculated, epididymal or testicular sperm may be selected based on presence of the sperm chaperone protein, and such sperm containing the chaperone protein are then injected into an egg to fertilize the egg. Alternatively, a sperm fraction may be selected based on presence of the sperm chaperone protein, and such sperm fraction containing the chaperone protein are then used to fertilize an egg.

Yet another aspect of the present invention provides a method of contraception in women comprising: providing sperm; binding one or more antibodies specific to a protein accessible on individual sperm or the sperm tail; and inhibiting movement of sperm to which is bound the one or more antibodies, thereby inhibiting fertilization by the antibody-bound sperm. One or more of the antibodies may be bound to protein accessible on individual sperm tails. Preferably, one or more antibodies are bound to chaperone protein present on plasma membrane of sperm. More preferably, a portion of the sperm contains testis-specific chaperone protein, antibodies specific to the sperm chaperone protein which are bound to individual sperm containing the chaperone protein, leaving individual sperm not containing chaperone protein free of the antibodies, and movement of sperm to which is bound antibodies specific to the sperm chaperone protein is inhibited. Such a method may be conducted by introducing selected epitope peptides of the chaperone protein into the female reproductive tract for the systemic generation of chaperone protein antibodies to arrest sperm motility, by introducing into the reproductive tract anti-chaperone protein antibodies in order to diminish sperm motility and fertilization potential, or by introducing into the female reproductive tract sperm barriers containing an active component of anti-chaperone protein antibodies or other antibodies directed to sperm plasma membrane proteins which are able to capture and arrest sperm and diminish fertilization potential. The sperm barriers may be intrauterine or intracervical devices.

In all of the above methods, where the sperm is human sperm, the chaperone protein is preferably HspA2. Where the sperm is non-human sperm, the chaperone protein is a variant testis-specific chaperone protein.

A further aspect of the present invention provides a multi-part system for determining the quality or fertilization potential of a sperm sample by detecting and measuring amount of testis-specific chaperone protein in the sperm, wherein an increased amount of the chaperone protein indicates a higher chance of fertilization by the sperm. In one embodiment the system comprises a sperm washing solution; a sperm homogenization solution; a composition containing an antibody specific to the sperm chaperone protein; and a composition capable of visually distinguishing any of the antibody which is bound to the sperm chaperone protein. In another embodiment, the system comprises a sperm washing solution; a sperm homogenization solution; a composition adapted to detect ATP bound to the sperm chaperone protein; and a composition capable of visually distinguishing any of the ATP which is bound to the sperm chaperone protein.

DESCRIPTION OF THE PREFERRED EMBODIMENTS

The Testis-Specific Chaperone Protein

The present invention provides an improvement to the method disclosed in the aforementioned U.S. Pat. No. 4,945,044, the disclosure of which is hereby incorporated by reference. An objective biochemical method is provided based on the measurement of the testis-specific chaperone protein ("CP"). In humans, the testis-specific chaperone protein is believed to be HspA2 testis-specific chaperone protein. In rodents, the homologue testis-specific chaperone or heat-shock protein is believed to be HSP70-2 chaperone protein. The chaperone protein is also present in the sperm of other species, such as in horse sperm, and its particular identity may be determined without undue experimentation. The terms "chaperone protein" or "CP" as used herein also includes variants of the protein.

As a result of testing of 1- and 2-dimensional SDS-polyacrylamide gel electrophoresis, amino acid sequencing, immunocytochemistry of the testicular tissue and of mature sperm, it has unexpectedly been determined that the CK-X isoform comprises the aforementioned chaperone protein, e.g., HspA2 in men, as a developmentally regulated marker of sperm maturity and function. The present invention is based on the discovery that the chaperone protein biochemical marker, HspA2 in men, reflects the cellular maturity of spermatozoa and provide a method of monitoring sperm maturation. In rodents the importance of HSP70-2 has been demonstrated by the selective destruction of the HSP70-2 gene. The HSP70-2 knock-out mice showed diminished sperm concentrations and increased sperm DNA degradation.

It has also been found that the electrophoretic properties of HspA2 are similar to those of the muscle CK-M on the native Agarose gels of the type used for CK isoform analysis. Moreover, the assay system for CK activity also detects adenosine triphosphate (ATP) synthesis, so that the ATP which binds the HspA2 chaperone may be perceived as new ATP produced. The fact that the chaperone protein has bound ATP is important from the point of view of sperm chaperone protein ratio measurements because this ATP can be measured and distinguished from the ATP which is generated by the sperm CK-B in the presence of the creatine phosphate and ADP substrates.

Detecting and Measuring Amount of Testis-Specific Chaperone Protein

In addition to determining that testis-specific chaperone protein is important in determining sperm quality, the present invention provides a method for testing sperm maturity by detecting the levels of chaperone protein, and determining the chaperone protein ratio, in sperm samples.

There are several approaches for the measurement of chaperone protein ratio, which is a measure of the amount of sperm chaperone protein versus sperm mass of the sample. Assessment of sperm mass may be based on sperm concentrations, sperm CK-B or other sperm cytoplasmic protein, total sperm protein, sperm DNA content or other factors. Three approaches have been preferably identified for chaperone protein assessment: i) immuno assay with chaperone protein antibodies; ii) enzymatic determination of the sperm ATP, with and without CK substrate, in order to measure the chaperone protein-bound ATP versus ATP generated by the sperm CK-B, and iii) chemical measurements of the chaperone protein-bound ATP in sperm. The first approach determines the amount of chaperone protein by binding one or more antibodies specific to the sperm chaperone protein to the sperm and measuring the antibody content. The second and third approaches measure ATP bound to the sperm chaperone protein.

The steps of the chaperone protein ratio assessment preferably include: 1) measurement of sperm chaperone protein concentrations; 2) determination of sperm concentrations or sperm mass using CK-B, another cytoplasmic protein, total sperm protein, sperm DNA or other factors that reflect sperm numbers in the test aliquot; and, finally, 3) using two sets of data as a basis for determining the chaperone protein ratio sperm maturity parameter. Measurements of the levels of chaperone protein and sperm mass may be carried out by computer assisted semen analysis, by immuno assay and fluorescence techniques, by the ATP associated with chaperone protein and ATP generated by the CK-B, respectively, or by colorimetry, immunocytochemistry or other immuno-techniques, enzymatic measurements, fluorescent labeling and cell sorting.

The method for the detection of sperm chaperone protein concentrations and chaperone protein ratios or the ratios of CP/sperm concentrations, CP/sperm cytoplasmic proteins or CP/sperm DNA in semen is composed of the phases of the chaperone protein determination and of the denominator factors of sperm concentrations, concentrations of CK-B or other cytoplasmic proteins, total sperm protein, or sperm DNA content. The detection of the chaperone protein may be carried out by immunoassay, by an enzymatic approach and by a chemical method of ATP detection using the luciferase bioluminescence assay. These varieties of methods are all aimed at the determination of the expression level CP/(CK-B+CP) which is the measure of sperm maturity and fertilizing potential as described above.

Proper specimen collections and washing of the sperm for removal of seminal fluid is important to obtain an accurate interpretation of chaperone protein and sperm mass analysis. If the determination is not carried out immediately after collection, the washed sperm pellet covered with a buffer containing an —SH group protectant should be refrigerated and it may be stored at 4° C. Alternatively, for long-term storage, the sperm pellets may be kept at −70° C. Repeated freezing and thawing destroys protein structure and should be avoided.

The determination of chaperone protein ratio may also be accomplished by the chemical measurements, for instance with the luciferase which may measure chaperone protein-bound ATP, after a metabolic inhibitor is added to the sperm and to the sperm extract in order to inhibit the de novo ATP production. Alternatively, the chemiluminescent detection may be performed following electrophoretic separation of the chaperone protein-ATP complex and of the CK-B. The detection and scanning, as well as the integration of the signals, are now automated and readily available as workstations.

For the detection of chaperone protein and CK-B, which represents the sperm mass, one can also use an enzymatic method. This is based on the fact that the chaperone protein-bound ATP may be directly detected by the NAD/NADH system, whereas ATP generation by the CK-B will occur only in the presence of the CK-B substrates, ADP and creatine phosphate. Thus, the difference between ATP measured in the sperm extracts in the absence and presence of the substrates will provide the concentrations of the two factors necessary for the chaperone protein ratio measurement, chaperone protein and CK-B. The detection may occur in microplates, slides or on Agarose gels which are compatible with plate or slide readers. The sperm proteins may be spotted in two wells, or they can be separated by electrophoresis in an agarose plate or other medium.

For the detection of the total sperm ATP (comprised of the chaperone protein-bound and CK-B generated ATP), the sperm extract is overlaid with the ATP detection substrate. CK catalyzes the transfer of phosphate from creatine phosphate to an adenosine diphosphate (ADP) forming creatine and adenosine triphosphate (ATP). The ATP formed in the CK reaction is used to produce glucose-6-phosphate. This reaction is catalyzed by the enzyme hexokinase. The glucose-6-phosphate is then oxidized by the enzyme, glucose-6-phosphate dehydrogenase with a simultaneous reduction of nicotinamide adenine dinucleotide (NAD) to the fluorescent derivative, NADH. The NADH fluorescence, which is proportional to the presence of chaperone protein-bound plus CK-B generated ATP, is quantified on agarose plates by a scanning fluorometer. In measurement of the ATP bound to chaperone protein alone, the ATP is directly available for glucose-6-phosphate synthesis, leading to production of the respective NADH fluorescence signal which represents the chaperone protein concentration alone, and may be deducted from the total ATP signal to provide the ATP generated by the CK-B. The amounts of chaperone protein-bound and CK-B generated ATP are proportional to the content of these proteins in the sperm extract and provide the chaperone protein ratio expressed as %CP/(CP+CK-B).

In addition to the chaperone protein measurement in sperm extracts, due to the development of chaperone protein specific antibodies, one can detect chaperone protein expression in individual mature sperm by chaperone protein-specific antibodies, which allows the assessment of the proportion of mature sperm in semen samples of sperm fractions tested, or in tissue or body fluid extracts. This method can be also adapted as a feature for a computer assisted semen analyzer which then in addition to sperm concentration, motility, velocity and other parameters will provide the percent of mature sperm in a specimen.

EXAMPLE

Sample preparation includes (a) obtaining and preparing a sperm sample in a test tube or vial, (b) adding to the sample by centrifugation a sperm washing solution while agitating, and (c) concentrating the washed sample by centrifugation to obtain a sperm pellet. A homogenizing solution is then added to the pellet and (d) homogenized with a stirrer or plunger to produce (e) a sperm homogenate. The sperm homogenate is then (f) centrifuged to clarify it. A pipette is used to take an aliquot of the sperm supernatant extract which is then (g) deposited in separate wells for the determination of the chaperone protein content by the immuno assay in a well plate and a sandwich non-competitive immunoassay may be carried out using monoclonal or polyclonal chaperone protein antibodies.

With respect to the ATP-based detection method, the intrinsic NADH fluorescence arises from the chaperone protein-bound ATP and of the CK-B generated ATP which is combined in a well which also contains the CK substrate with ADP and creatine phosphate. In addition to the sperm concentrations or sperm mass, one may perform measurements of CK-B content, CK-B generated ATP, other sperm cytoplasmic proteins, such as LDHC4 or glucose-6-phosphate-dehydrogenase, total sperm protein content or DNA concentrations, which are all proportional to the sperm protein mass or the number of sperm in the sample. Thus, the ratio of %CP/(CK-B+CP), CP/total protein or CP/DNA in different embodiments of the patterns are measurements of the sperm chaperone protein levels which are, along with sperm concentration measurements, equally applicable for the performance of the chaperone protein ratio or chaperone protein level measurements reflecting sperm maturity.

The preferred procedures for testing sperm samples or fractions according to the method of the present invention is as follows:
1) Determination of the sperm chaperone protein concentration by immunoassay;
2) Determination of the chaperone protein-bound and CK-B generated ATP by an enzymatic approach, using the difference in NADH flourescence signal in the absence and presence of a CK substrate, respectively; or
3) Determination of the sperm ATP by a chemical approach (after adding a mitochondrial blocker in order to arrest internal ATP production) using the luciferase ATP detection system on whole sperm extracts or after separation of the chaperone protein and CK-B with the methods of immuno-assessment. In case of the sperm ATP measurements by luciferase, instead of chaperone protein ratio, one measures the sperm maturity level parameter which is expressed as chaperone protein concentration/sperm mass. The sperm mass may be measured by the sperm concentration, any of the sperm cytoplasmic proteins, total sperm protein or by the sperm DNA content which is proportional with the sperm concentrations.

Sample Preparation

The preferable sample preparation process with respect to sperm extraction is identical in all three approaches of sperm maturity measurements. (1) The sperm should be separated from the seminal fluid and washed in the sperm washing solution as soon as possible after liquefaction (about 60–90 minutes after collection); (2) The sperm pellet after washing and centrifugation should be homogenized (10 turns with the stirrer or plunger), or vortexed for 30 seconds in 0.2 ml of homogenization solution; (3) The sperm homogenate is clarified by centrifugation, and aliquots of the sperm extract supernatant are subjected to the studies.

If the test cannot be run within 3 hours of collection, the sperm pellet should more preferably be overlaid by about 0.2 ml homogenization solution so that it may be stored refrigerated for three days or frozen (at −70° C.) for up to two months. Repeated freezing and thawing will inactivate the enzyme and should be avoided.

The present invention provides a system for the determination of sperm maturity and fertilizing potential which may be packaged in kit form. The test system and kit is intended to be used by andrology laboratories, and by specialty offices of urologists and fertility specialists. Such kits may contain sperm washing and sperm homogenization solutions to prepare the sperm samples for detection of sperm containing the chaperone protein. Preferably, the sperm test method of the present invention utilizes a kit composed of two concentrated generally applicable reagents (sperm washing solution and sperm extraction solution) which may be reconstituted prior to use with the addition of distilled water, and a 15 ml graduated conical test tube with matching plunger which is used for homogenization.

Where the chaperone protein is to be determined by measuring ATP bound to the sperm chaperone protein, the kit contains a composition adapted to detect ATP bound to the sperm chaperone protein, such as a chaperone-protein-specific immuno-assay. The kit also contains a composition capable of visually distinguishing any of the ATP which is bound to the sperm chaperone protein. This may then be read by a conventional plate reader. Due to the multiple sample handling capabilities of some existing plates and plate readers, the use of the enzyme-linked immuno assays, the combination of immuno labeling and cell sorting and other related technologies, the chaperone protein ratio assays may also be used in mass screening and monitoring of men for sperm maturity and fertilizing potential.

Where the chaperone protein is to be determined by binding one or more antibodies specific to the sperm chaperone protein and measuring the antibody content, the kit preferably contains a composition containing an antibody specific to the sperm chaperone protein. In order to distinguish and count the antibodies specific to the sperm chaperone protein, the kit also contains a composition capable of visually distinguishing any of the antibody which is bound to the sperm chaperone protein.

Other reagents that are applicable to the three specific methods of chaperone protein determination (chaperone protein immuno assay, chaperone protein-bound and CK-B generated ATP measurement, and ATP determination by bioluminescence) are described below in connection with the particular technology, and are amenable for packaging in kits along with the microplates with multiple wells, detection aids and other supplies that are useful in performing the assays. Similar information is provided for the reagents necessary for the electrophoretic step, if one desires to separate the chaperone protein and CK-B prior to the detection of the chaperone protein-bound and CK-B generated ATP, or to perform the respective bioluminescent luciferase ATP assessment.

Reagents

1) Sperm washing solution (Phosphate buffer-normal [0.15M]saline, pH:7.01)
2) Sperm homogenization and extraction solution (Phosphate buffer-normal saline, pH:7.0, 20 mM DTT, 0.10% Triton).
3) ATP/NADH ATP developer solution, with and without CK substrate for the measurement of the chaperone protein-bound and CK-B generated ATP.
4) Electrophoretic buffer solution: MES (2-(N-Morpholino) ethane sulfonic acid) pH 6.2.
(Composition of the reagent for the detection of chaperone protein-bound and CK-B generated ATP (for the chaperone protein-bound ATP determination, the Creatine Phosphate and ADP are omitted.)

TABLE 1

Active Ingredient Concentration

| Active Ingredients | Final Concentration In Reagent |
| --- | --- |
| Creatine Phosphate | 90 mM |
| Adenosine Diphosphate | 12 mM |
| Magnesium $^{+2}$ | 60 mM |
| Adenosine Monophosphate | 15 mM |
| Nicotinamide Adenine Dinucleotide | 6 mM |
| Glucose | 60 mM |
| NAC | 60 mM |
| Hexokinase | $9 \times 10^3$ IU/L (30° C.) |

TABLE 1-continued

Active Ingredient Concentration

| Active Ingredients | Final Concentration In Reagent |
| --- | --- |
| Glucoste-6-phosphate Dehydrogenase | $7.5 \times 10^3$ IU/L (30° C.) |

ATP Measurement in Sperm Extracts

The procedure for the detection and measurement of the chaperone protein-bound and CK-B generated ATP is as follows: 1) place aliquot pairs of 1, 3 and 5 µl of sperm extract side-by-side in micro wells, on gel plates or other transparent medium. 2) Evenly dispense 1 ml of reagent onto the surface of the medium. Make sure that there is enough space between the sperm extract spots that the reagents containing or lacking CK substrate do not mix. 3) For the detection of the CK-B generated ATP, place the micro well or other platform with the sample (sample side up) in prewarmed incubator tray on moistened blotting paper and incubate the plate at 37° C. for 20 minutes. 4) Following incubation, place the medium in a drying incubator/oven. Dry for 15–20 minutes or until dry. 5) Inspect the dried sperm spots under ultraviolet light at 365 nm. 6) Scan the sperm spots using a photometric scanner with excitation wavelength of 365 nm and which detects the emission wavelength at 460 nm.

Electrophoresis Procedure

If the electrophoretic separation of the chaperone protein and CK-B is practiced using the Helena Laboratories reagents and workstation, the following procedure is preferably employed: 1) Place the reconstituted MES buffer in each chamber of the electrophoresis cell. Level the buffer in both chambers, wipe moisture off center partition. 2) Gently peel the agarose or cellulose acetate electrophoresis plate from its hard plastic cover, being careful to handle the film only by its edges. 3) Apply three different aliquots of the sample to three sample wells (typically 0.001, 0.002, 0.005 ml) to provide allowance for chaperone protein concentration and CK-B activity differences in the various samples. Samples should be applied using a quantitative microliter dispenser and disposable sample tip. Use a fresh tip for each sample. Touch the drop to the well; do not touch the pipette tip to the well or the plate surface. Apply samples as quickly as possible. After sample application, allow the sample to diffuse into the agarose for one minute. 4) Insert the loaded agarose film into the electrophoresis cell agarose side down, matching the anode (+) side of the cell and (5) Turn on power supply, adjust it to provide adequate current. Typically, 90 volts is used and 20 minutes is allowed for the electrophoresis. 6) Following the electrophoresis, drain the excess buffer from the cell, grasp the agarose film by its edges and remove it. Place the film, agarose side up on a flat counter top with the cathode (−) edge toward you. 7) Blot residual buffer from the end of the agarose with a single folded wipe along the gel. 8) Proceed with development of the NADH fluorescent signal proportional with the chaperone protein-bound ATP and CK-M generated ATP, as described above, using the CK-B substrate reagent available pre-packaged from the manufacturer.

Chaperone Protein Concentration Determination by Sandwich Enzyme Linked Immuno Assay Utilization of the human sperm chaperone protein antibody facilitates the sperm chaperone protein concentration determination by ELISA. A typical assay may be carried out as follows:

Solution Preparation

Coating Solution: Antigen or antibody are diluted in coating solution to immobilize them to the microplate. Commonly used coating solutions are: 50 mM sodium carbonate, pH 9.6; 20 mM Tris-HCl, pH 8.5; or 10 mM Phosphate-buffered saline (PBS), pH 7.2.

Blocking Solution: Commonly used blocking agents are: BSA, nonfat dry milk, casein, gelatin, and the like.

Primary/Secondary Antibody Solution: Primary/secondary antibody should be diluted in 1×blocking solution to help prevent non-specific binding.

Antigen Solution: Sperm extract should be diluted in 1×blocking solution to help prevent non-specific binding Wash Solution: Typically 0.1 M PBS or Tris-buffered saline (pH 7.2) with a detergent such as Tween 20 (0.02%–0.05% v/v).

Procedure

1) Coat the capture antibody (human sperm chaperone protein antibody in this case) at 100 ng/well in PBS on a Nunc Maxi Sorp plate or similar. The concentration of the capture antibody should be constant in all test wells. Incubate 8 hours at 4° C. or 1 hour at 37° C.
2) Block the wells with 1% BSA or 1% Non Fat Dried Milk, 300 µliters//well. The concentration of the blocking solution should be constant. Incubate 30 to 60 min. at room temperature.
3) Wash wells 2× with PBS/0.05% Tween 20 (wash buffer)
4) Add a 5× serial dilution of the sperm extract in blocking solution to the wells. Incubate 30 min. at room temperature.
5) Wash 5× with Wash Buffer.
6) Add chaperone protein (detecting) antibody or conjugated (color generating) detecting antibody to the wells. The concentration of the antibody used, the incubation time and temperature and other experimental details may vary with different antibodies. The antibody conjugate is generally an enzyme that converts a colorless substrate into a colored byproduct.
7) Wash 5× with wash buffer.
8) Add the conjugated secondary antibody (to bind the non-conjugated primary antibody added in the previous step) if this applies.
9) Wash 5× with wash buffer.
10) Develop the plate by adding the appropriate substrate for the development of color in the wells, and stop the enzymatic reaction when the negative controls are just faintly detectable.
11) Read the plate with a microplate reader at appropriate wavelength (depending on the conjugate and respective substrate).
12) Note: Appropriate positive and negative controls are necessary in order to verify the validity of the assay and monitor the quality of the reagents used.

Determination of Sperm Chaperone Protein by Bioluminescence

The determination of the chaperone protein-bound ATP in human sperm extract may be carried out by quantitative bioluminescence with firefly luciferase and its substrate, luciferin. In performing the assay there are three special precautions it is preferable to observe: 1) Add mitochondrial inhibiting agents, such as sodium azide, to the sperm washing solution and to the sperm extract in order to block internal sperm ATP production. 2) Protect luciferin and luciferase from light as much as possible. 3) Be very gentle with the luciferase containing solutions because the enzyme denatures easily.

Preferred equipment and reagent solutions: Luminometer, luciferin in reaction buffer (25 mM Tricine buffer, PH: 7.8, 5 mM $MgSO_4$, 0.1 mM EDTA, 2 mM sodium azide), DTT and ATP standard solution.

Assay reagents: Reaction buffer containing 1 mM DTT, 0.5 mM luciferin, 2 µg/ml luciferase; ATP standard solution in distilled $H_2O$.

Procedure

1) Place standard assay solution in luminometer and measure background luminescence.
2) Start the reaction by adding known amounts of ATP, and generate a standard curve after deducting the background luminescence from each point. Be sure that the volume of ATP solution is <10% of the assay volume.
3) Add sperm extract in a volume equal to that of the standard curve sample.
4) Calculate the amount of ATP in the sperm extract based on the standard curve.

Determination of the Sperm Mass for the CP/sperm (or Sperm Mass Level)

The CP/sperm level may be calculated based on the sperm concentration of the sample (determined visually or with computer assisted semen analysis), based on cytoplasmic protein content (the enzymes used for this purpose so far were the CK-B, LDHC4, and glucose-6-phosphate dehydrogenase), total sperm protein content, and colorimetric measurement of sperm DNA with thiazine blue or similar reagent by standard methods.

While not wishing to be bound by theory, it is believed that the predictive value of the chaperone protein concentration and chaperone protein ratio determinations in sperm is due to the fact that during the last phase of sperm development, called spermiogenesis, the sperm are remodeled in both the intracellular compartment (measured by the expression of chaperone protein) and in the sperm plasma membrane (MRD, zona, GT). The latter facilitates the development of the binding site(s) of sperm for the outer layer of oocyte, the zona pellucida. Immature sperm which do not express chaperone protein, and do not complete plasma membrane remodeling and cytoplasmic extrusion, are deficient in zona pellucida binding. They also contain retained cytoplasm, which is extruded from normally developed mature sperm, and carry high levels of reactive oxygen species which are damaging to the sperm DNA (MRD, zona, LP). Further, chaperone protein is also a participant of the meiotic process, a genetically regulated cleavage and rebuilding of DNA during sperm development. In the absence of chaperone protein, the DNA rebuilding is apparently faulty, and in immature sperm DNA integrity is diminished and there is an increased incidence of chromosomal aneuploidy. These factors cause diminished sperm fertilization potential, as well as errors in early zygotic development, which collectively lead to a higher risk for the demise of the conceptus. Thus, the level of HspA2 in men is predictive for the ability of sperm sample to cause and support pregnancy.

With regard to DNA integrity, peroxidative cleavage of sperm DNA is of concern because it is associated with increased rates of childhood cancer in the offspring of chronic smokers. In order to study the extent of DNA fragmentation in mature and diminished maturity sperm, there have been used the combined methods of in vitro decondensation and in situ nick translation in 150 samples. The latter method is based on enzymatic repair of the DNA strands using DNA basis to which a reporter alkaline phosphatase molecule is attached. There was found to be a significant percentage increase in the incidence of sperm with DNA fragmentation among the diminished maturity sperm fractions. The relationship between the sperm maturity and DNA fragmentation was demonstrated by the significant correlation between the incidence of sperm with extensive DNA degradation and the decline of the chaperone protein ratio parameters. Thus, chaperone protein concentrations, and the chaperone protein ratio in sperm, have been found to measure not only sperm maturity, but of the rate of lipid peroxidation and the extent of DNA fragmentation as well.

Also studied was the issue of whether due to the lack of chaperone protein in sperm during the meiotic process, there is a relationship between diminished sperm maturity and an increased incidence of numerical and structural chromosome abnormalities. More specifically, it was examined whether there is a higher frequency of disomies, i.e., an extra second chromosome, or diploidies, i.e., two sets of chromosomes, instead of one which is normal for germ cells. There were utilized multicolor fluorescence in situ hybridization (FISH), using chromosome probes, in the diminished maturity and mature sperm fractions of semen samples prepared by centrifugation through 28% and 80% Percoll gradients. (The 28% pellet contains larger, immature sperm with cytoplasmic retention, sperm that are excluded by 80% Percoll). In two experiments 60,000 spermatozoa were examined (44,000 in one, and 16,000 in the other). Reflecting the differences in sperm maturity, the incidence of sperm with high CK content due to immaturity and cytoplasmic retention were about 25.6±8.0% and 5.5±1.2%. For detection of autosomal disomy and diploidy, two-color FISH to chromosomes 10, 11, and 17, and multicolor FISH for scoring X and Y were utilized. The incidence of chromosomal abnormalities was higher in the immature vs. the mature sperm fractions. The frequencies of disomies were (%): 17:0.4 vs. 0.1; XY: 0.53 vs. 0.12; Y: 0.26 vs. 0.03 ($p<0.0001$ in all); 10:0.23 vs. 0.13 ($p<0.01$); 11:0.22 vs. 0.11; and X: 0.16 vs. 0.13 vs. (NS). The diploidy frequency was also increased (%): 10,10/11,11: 0.69 vs. 0.38; 17,17/(X,X),(Y,Y): 0.71 vs. 0.33 ($p<0.0001$ in both). The data indicate that sperm of diminished maturity show a substantially increased incidence of chromosomal abnormalities. In order to establish that the aneuploidies indeed originated in immature sperm, there has also been shown a significant relationship ($r=0.64$, $p<0.01$) between the incidence of aneuploidies and the incidence immature sperm with cytoplasmic retention and the frequency of aneuploidies in 8 pairs of sperm fractions. These samples demonstrated the extent of DNA cleavage in sperm of normal and diminished maturities. Thus, chaperone protein concentrations or chaperone protein ratios were confirmed to predict the numerical aberrations of sperm chromosomal content.

It is believed that the function of chaperone protein is the facilitation of protein folding and delivery within the cell. These functions, and the timing of the chaperone protein expression which occurs during cytoplasmic extrusion and sperm membrane remodeling in the terminal stage of sperm development, implies that the chaperone protein is important in the maturation process of sperm. Significantly, it is believed that the presence of the chaperone protein in sperm signifies a completion of proper sperm development. Thus, the cytoplasmic retention and a low level remodeling of the plasma membrane (sufficient to cause a diminished formation of the zona-binding site) is likely related to the lack of chaperone protein in immature sperm. Chaperone protein expression provides a measure of sperm maturity in sperm fractions, and identification of individual mature sperm by the virtue of chaperone protein expression. Thus, the chaperone protein ratios reflect the proportion of mature, fertile sperm versus the diminished maturity sperm subpopulations in ejaculates and in sperm fractions. Also, antibody to the chaperone protein has been shown to diminish sperm motility. This demonstrates the contraceptive potential of chaperone protein, after immunization of women and animals with an antibody specific for an epitope of sperm chaperone protein or other sperm protein.

In addition to fertility studies, the utility of the chaperone protein ratio measurements permit the assessment of changes in sperm maturity and quality, before the decline of sperm concentrations, and it may be used as an effective screening procedure in an industrial setting, or in the military, where men are exposed to reproductive toxicity or after they are removed from the toxic environment. The chaperone protein ratio measurements will also permit the monitoring of spermatogenesis in male patients who are treated with various fertility and enhancement drugs and during aging. Also, the suppression of spermatogenesis or sperm maturation can be monitored in conjunction with male contraceptive techniques, in which hormone or peptide analogues temporarily reduce or alter spermatogenesis. After the termination of such treatments, sperm chaperone protein concentrations will indicate the resumption of normal spermatogenesis, and will monitor whether the sperm quality in a particular man has reached that of the pretreatment levels. Determination of chaperone protein concentrations in accordance with the present invention can also be used to describe the quality of sperm in animals, such as stallions and bulls, and in order to predict fertilizing potential and breeding proficiency.

As the phrase is used herein, a "higher sperm quality" refers, in general, to sperm which has: i) a higher chance of fertilization of an egg, ii) greater maturity, iii) greater ability to bind to the zona pellucida of oocytes, iv) lower DNA fragmentation, v) higher DNA integrity, vi) low level of chromosomal aneuploidy and vii) greater ability to maintain viability following cryopreservation and thawing.

Thus, the present invention provides a useful and long sought method to provide quantitative assessment of sperm quality, e.g., maturity and fertilizing potential, based on objective biochemical sperm parameters alone, such as the ratio of the chaperone protein to the total of the chaperone protein and CK-B isoforms within a single ejaculate. Following determination of the sperm quality parameter, sperm fractions having the predetermined minimum level of chaperone protein ratio >10% can be selected for attempts to fertilize human eggs by in vivo or in vitro techniques, such as swim-up selection, sperm self migration, or various column separation and density gradient centrifugation, and other sperm selection techniques prior to fertilization attempts.

Screening Sperm Containing Testis-Specific Chaperone Protein

Due to the antibodies specific to chaperone protein, which is present in on the surface of the tail of mature sperm, one is able to screen sperm for the expression of chaperone protein in ejaculated semen or in germ cells arising from any part of the male, or, after introduction of sperm of the female reproductive system in human individuals and in animals. Semen samples which meet a predetermined minimum sperm maturity level, as detected by the chaperone protein ratio, is classified as mature sperm fraction or a sperm population having a high chance of fertilization and the semen sample is selected for use in vivo or in vitro fertilization attempts on eggs. Chaperone protein expression may also be detected in a single individual sperm for diagnostic evaluation indicate the proportion of mature sperm in aliquots of semen or sperm fractions.

In screening the sperm based upon presence of the sperm chaperone protein, one or more individual sperm containing the chaperone protein may be segregated and removed from the sample and then injected into an egg to fertilize the egg. Screening may also be population-based by segregating and selecting a sperm fraction by gradient centrifugation, swim-up, cell sorting or other methods based on the properties of mature versus diminished maturity sperm or by presence of the sperm chaperone protein, with the sperm fraction containing the chaperone protein then being used to fertilize an egg.

Contraception Based on Sperm Chaperone Protein

Additionally, one or more contraception methods may be based on use of the testis specific chaperone protein or other protein accessible on individual sperm. To prevent conception, one or more antibodies specific to a protein on the surface of or otherwise accessible on individual sperm can be bound to that protein by introducing the antibody into the female reproductive tract, e.g., as a coating on an intrauterine or intracervical or other device which may act as a sperm barrier. Hyaluronic acid or a salt thereof, as disclosed in U.S. Pat. No. 5,897,988 (the disclosure of which is hereby incorporated by reference) may also be used as a coating on such intrauterine or intracervical or other devices to capture the sperm by the sperm hyaluronic acid receptors. The antibodies then become bound to the surface of the sperm in the female reproductive tract and inhibit movement of sperm to which they are bound, thereby inhibiting fertilization of the egg by the antibody-bound sperm. This contraception method is particularly useful where the protein antibodies are bound to protein accessible on individual sperm tails, since tail movement is critical to sperm mobility and fertilization.

Antibodies are bound to chaperone protein present on the plasma membrane of sperm. This then leaves individual sperm not containing chaperone protein free of the antibodies, and movement of sperm to which is bound antibodies specific to the sperm chaperone protein is inhibited. Such a method may be conducted by introducing selected epitope peptides of the chaperone protein into the female systemically or into the reproductive tract for the generation of chaperone protein antibodies, by introducing into the reproductive tract anti- chaperone protein antibodies, or by introducing into the female reproductive tract sperm barriers containing an active component of anti-chaperone protein antibodies or other sperm plasma membrane antibody. All of these methods are able to capture and arrest sperm and diminish fertilization potential of the egg by the sperm. Thus, the present invention achieves the advantages sought. It provides an improved method for testing of sperm quality, which also shows high correlation with fertilizing potential and occurrence of pregnancies. It further provide a method and kit for testing sperm quality which may be readily performed outside of a laboratory environment and at lower cost in physicians' offices.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of testing sperm quality comprising:
   obtaining a sample of sperm to be tested;
   detecting and measuring amount of testis-specific chaperone protein in the sperm sample by a chaperone protein-specific immuno-assay, wherein the testis-specific chaperone protein is selected from the group consisting of HspA2 testis-specific chaperone protein, and homologues thereof; and
   determining a sperm quality parameter relating the amount of the testis-specific chaperone protein measured in the sperm sample to amount of sperm in the sample wherein an increased amount of the chaperone protein per given amount of sperm in the sample indicates a higher sperm quality.

2. The method of claim 1 wherein the amount of sperm in the sample is measured by measuring sperm concentration, sperm cytoplasmic protein content, total sperm protein content or sperm DNA.

3. The method of claim 2 wherein a minimum sperm quality parameter is determined to be at least about 10 $\mu$g of the chaperone protein per mg of sperm protein, or per $10^8$ sperm.

4. The method of claim 1 wherein the amount of sperm in the sample is measured by measuring sperm DNA by colorimetry.

5. The method of claim 1 wherein the sperm is human sperm and the chaperone protein is human HspA2 chaperone protein.

6. The method of claim 1 wherein the sperm is non-human sperm and the chaperone protein is a homologue of HspA2 testis-specific chaperone protein.

7. The method of claim 6 wherein the non-human sperm is horse sperm.

8. The method of claim 1 wherein the sperm sample is obtained from ejaculated, epididymal or testicular sperm.

9. The method of claim 1 wherein the sperm quality parameter is used to predict a property selected from the group consisting of:
   sperm fertility independently from sperm concentration in semen;
   sperm maturity changes in men who are treated with male contraceptive methods, independently from sperm concentration in semen;
   sperm maturity changes in men who are exposed to reproductive toxicity, independently from sperm concentration in semen;
   extent of sperm cytoplasmic retention;
   sperm plasma membrane remodeling;
   ability of sperm to bind to zona pellucida of oocytes;
   sperm morphology;
   level of sperm lipid peroxidation;
   sperm DNA integrity or extent of sperm DNA fragmentation;
   frequency of sperm chromosomal aneuploidies;
   ability of sperm to maintain viability following cryopreservation and thawing; and
   combinations thereof.

10. A method of screening sperm for selection comprising:
    obtaining at least one sample of sperm to be tested;
    detecting amount of testis-specific chaperone protein in the at least one sample of sperm by testing a first sperm fraction of each said sample by a chaperone protein-specific immuno-assay wherein an increased amount of the testis-specific chaperone protein per sperm amount indicates a higher sperm quality, the testis-specific chaperone protein being selected from the group consisting of HspA2 testis-specific chaperone protein, and homologues thereof, selecting a quality sperm sample from the at least one sample, the selected sample having an indicated higher sperm quality; and selecting one or more individual sperm from a second sperm fraction of the selected sample.

11. The method of claim 10 wherein the chaperone protein is detected by binding one or more HspA2-specific antibodies to the sperm chaperone protein on sperm labeling the bound HspA2-specific antibodies, and observing the immuno-labeled sperm, visually or with automated, computer assisted semen analysis to detect the chaperone protein.

12. The method of claim 11 wherein the immuno-labeled sperm is detected in semen, in sperm fractions, in sperm smears, or in tissues or fluids of a male or a female reproductive tract.

13. The method of claim 10 wherein the step of selecting sperm includes selecting one or more individual ejaculated, epididymal or testicular sperm.

14. The method of claim 10 wherein the step of selecting one or more individual sperm from a second sperm fraction of the selected sample includes selecting a sperm fraction of the second sperm fraction.

15. The method of claim 10 wherein the sperm is human sperm and the chaperone protein is human HFspA2 chaperone protein.

16. The method of claim 10 wherein the sperm is non-human sperm and the chaperone protein is a homologue of HspA2 testis-specific chaperone protein.

17. The method of claim 16 wherein the non-human sperm is horse sperm.

18. The method of claim 10 further including exposing an egg to at least one of said one or more individual sperm selected from the second sperm fraction of the selected sample to fertilize the egg.

19. The method of claim 18 wherein the egg is exposed to the selected one or more individual sperm in vitro or in vivo.

20. The method of claim 19 wherein the egg is exposed to the selected one or more individual sperm by injecting the selected sperm into the egg in vitro.

21. A method of screening and segregating sperm comprising:

obtaining a sample of sperm to be tested;

detecting amount of testis-specific chaperone protein on a tail of one or more individual sperm in the sample by a chaperone protein-specific immuno-assay, the testis-specific chaperone protein being selected from the group consisting of HspA2 testis-specific chaperone protein, and homologues thereof; and segregating and removing from the sample one or more individual sperm with a detected higher amount of the testis-specific chaperone protein thereon, the one or more segregated individual sperm having an indicated higher sperm quality than those sperm with a lower amount of chaperone protein thereon.

22. A multi-part system for determining a quality or fertilization potential of a sperm sample by detecting and measuring amount of testis-specific chaperone protein selected from the group consisting of HspA2 testis-specific chaperone protein, and homologues thereof, in the sperm, wherein an increased amount of the chaperone protein indicates a higher sperm quality or a higher chance of fertilization by the sperm, the system comprising:

a sperm washing solution;

a sperm homogenization solution;

an antibody specific for the testis-specific chaperone protein to detect the testis-specific chaperone protein; and a composition for visually detecting any ATP which is bound to the testis-specific chaperone protein for determining the amount of testis-specific chaperone protein in the sperm sample.

* * * * *

UNITED STATES PATENT AND TRADEMARK OFFICE
CERTIFICATE OF CORRECTION

PATENT NO. : 6,541,206 B1
DATED : April 1, 2003
INVENTOR(S) : Gabor B. Huszar

It is certified that error appears in the above-identified patent and that said Letters Patent is hereby corrected as shown below:

Title page,
Item [56], OTHER PUBLICATIONS, 2nd citation, delete "Fertiliey" and substitute therefor -- Fertility --.

Column 2,
Line 66, delete "easured" and substitute therefor -- measured --.
Line 67, delete "easuring" and substitute therefor -- measuring --.

Column 3,
Line 1, delete "haperone" and substitute therefor -- chaperone --.

Column 11,
Line 23, before "300$\mu$liters//well" insert -- [blocking solutions] --.

Column 13,
Lines 31-36 were substituted as follows:
-- mature sperm fractions. The frequencies of disomies were (%): <u>17</u>: 0.4 vs. 0.1 ; <u>XY</u>: 0.53 vs. 0.12; <u>Y</u>: 0.26 vs. 0.03 (p< 0.0001 in all); <u>10</u>: 0.23 vs. 0.13 (p<0.01); <u>11</u>: 0.22 vs. 0.11; and <u>X</u>: 0.16 vs. 0.13 vs. (NS). The diploidy frequency was also increased (%): 10,10/11,11: 0.69 vs. 0.38; 17,17(X,X),(Y,Y): 0.71 vs. 0.33 (p<0.0001 in both). The data --.

Column 17,
Line 25, delete "HFspA2" and substitute therefor -- HspA2 --.

Signed and Sealed this

Twenty-ninth Day of July, 2003

JAMES E. ROGAN
*Director of the United States Patent and Trademark Office*